United States Patent
Baumann et al.

(10) Patent No.: US 9,917,265 B2
(45) Date of Patent: Mar. 13, 2018

(54) COPPER(I) COMPLEXES, IN PARTICULAR FOR OPTOELECTRONIC COMPONENTS

(75) Inventors: Thomas Baumann, Karlsruhe (DE); Tobias Grab, Karlsruhe (DE); Daniel Zink, Karlsruhe (EE)

(73) Assignee: CYNORA GMBH, Bruchsal (DE)

( * ) Notice: Subject to any disclaimer, the term of this patent is extended or adjusted under 35 U.S.C. 154(b) by 1110 days.

(21) Appl. No.: 14/129,707

(22) PCT Filed: Jun. 29, 2012

(86) PCT No.: PCT/EP2012/062783
§ 371 (c)(1),
(2), (4) Date: Mar. 6, 2014

(87) PCT Pub. No.: WO2013/001086
PCT Pub. Date: Jan. 3, 2013

(65) Prior Publication Data
US 2014/0183490 A1   Jul. 3, 2014

(30) Foreign Application Priority Data

Jun. 29, 2011 (EP) .................................. 11171921
Jul. 8, 2011 (EP) .................................. 11173369
Aug. 26, 2011 (EP) .................................. 11179099

(51) Int. Cl.
*H01L 51/00* (2006.01)
*C07F 9/50* (2006.01)
(Continued)

(52) U.S. Cl.
CPC .......... *H01L 51/0091* (2013.01); *C07F 1/005* (2013.01); *C07F 1/08* (2013.01);
(Continued)

(58) Field of Classification Search
None
See application file for complete search history.

(56) References Cited

FOREIGN PATENT DOCUMENTS

| JP | 2014522391 A | 9/2014 |
|---|---|---|
| WO | 2010149748 A1 | 12/2010 |
| WO | WO2010149748 | * 12/2010 |

OTHER PUBLICATIONS

International Search Report and Written Opinion of International Searching Authority for PCT/EP2012/062783 dated Nov. 7, 2012.
(Continued)

*Primary Examiner* — Nathan T Leong
(74) *Attorney, Agent, or Firm* — Ryan, Mason & Lewis, LLP

(57) ABSTRACT

The embodiments of the invention relate to copper(I) complexes of the formula A

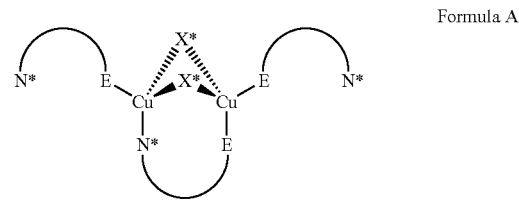

Formula A where
X* is Cl, Br, I, CN, SCN, alkinyl and/or $N_3$ (independently of one another),
N*∩E is a bidentate ligand with
  E being a phosphanyl/arsenyl group of the form $R_2E$ (in which R=alkyl, aryl, alkoxyl, phenoxyl, or amide),
  N* is an imine-function, which is a component of an N-heteroaromatic 5-membered ring that is selected from the group consisting of pyrazole, isoxazole, isothiazole, triazole, oxadiazole, thiadiazole, tetrazole, oxatriazole or thiatriazole,
  and "∩" is at least one carbon atom, which is likewise a component of the aromatic group, the carbon atom being located directly adjacent both to the imine nitrogen atom as well as to the phosphorus or arsenic atom.

The copper(I) complexes may be used in optoelectronic components, particularly in organic light emitting diodes (OLEDs).

12 Claims, 11 Drawing Sheets

Crystal structure of 2a:

(51) Int. Cl.
*C07F 1/00* (2006.01)
*C07F 1/08* (2006.01)
*H01L 51/50* (2006.01)

(52) U.S. Cl.
CPC .......... *C07F 9/5045* (2013.01); *H01L 51/009* (2013.01); *H01L 51/5016* (2013.01); *Y02E 10/549* (2013.01); *Y02P 70/521* (2015.11)

(56) References Cited

OTHER PUBLICATIONS

G.V. Oshovskii et al., "Thiadiazolylphosphines with Nitrogen Containing Substituents," Chemistry of Heterocyclic Compounds, Oct. 1997, pp. 1242-1243, vol. 33, No. 10.

E.V. Zarudnitskii et al., "C-Phosphorylation of 1,2,4-Triazoles with Phosphorus(III) Halides. Synthesis of 4,5-Dihydrobenzo[e][1,2,4]Triazolo[5,1-c][1,4,2]Diazaphosphinine Derivatives," Heteroatom Chemistry, Jan. 2002, pp. 146-152, vol. 13, No. 2.

G. Guillerm et al., "No. 503.—Cycloaddition Dipolaire 1-3 de Diazoalcanes sur des Composes Alcynyles des Groupes IVB, VB et VIB," Bulletin de la Societe Chimique de France, Jan. 1973, pp. 2739-2746, vol. 9-10, No. 2.

A. Igau et al., "Analogous a,a'-Bis-Carbenoid Triply Bonded Species: Synthesis of a Stable λ3-Phosphinocarbene-λ5-Phosphaacetylene," American Chemical Society, Sep. 1988, pp. 6463-6466, vol. 110, No. 19.

D.M. Zink et al., "Experimental and Theoretical Study of Novel Luminescent Di-, Tri-, and Tetranuclear Copper Triazole Complexes," ACS Publications, Organometallics 2011 American Chemical Society, pp. 3275-3283, vol. 30.

A.A. Tolmachev et al., "Chemistry of Heterocyclic Compounds," Sep. 1999, pp. 1117-1119, vol. 35, No. 9.

* cited by examiner

Figure 1: Crystal structure of 2a:
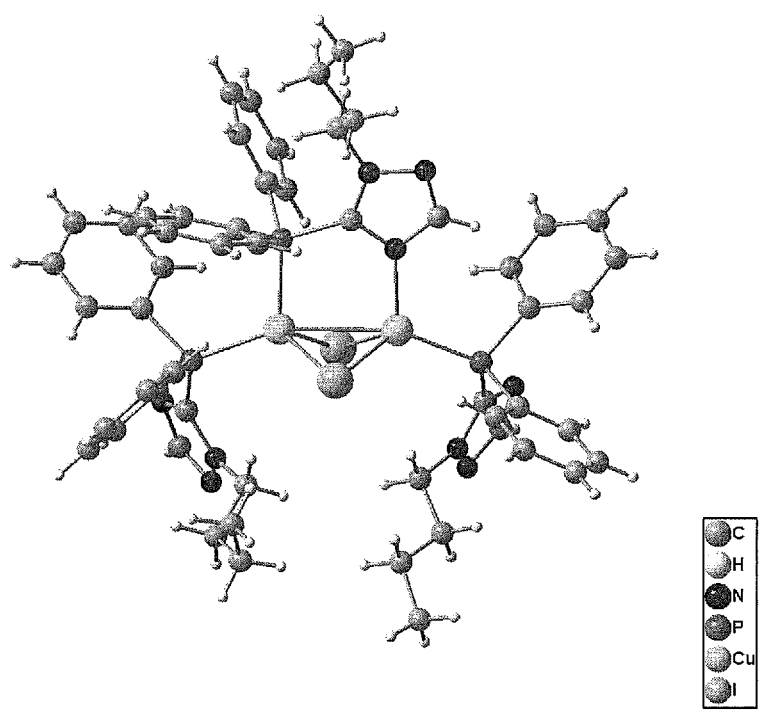

Figure 2: Emission spectrum of 2a:
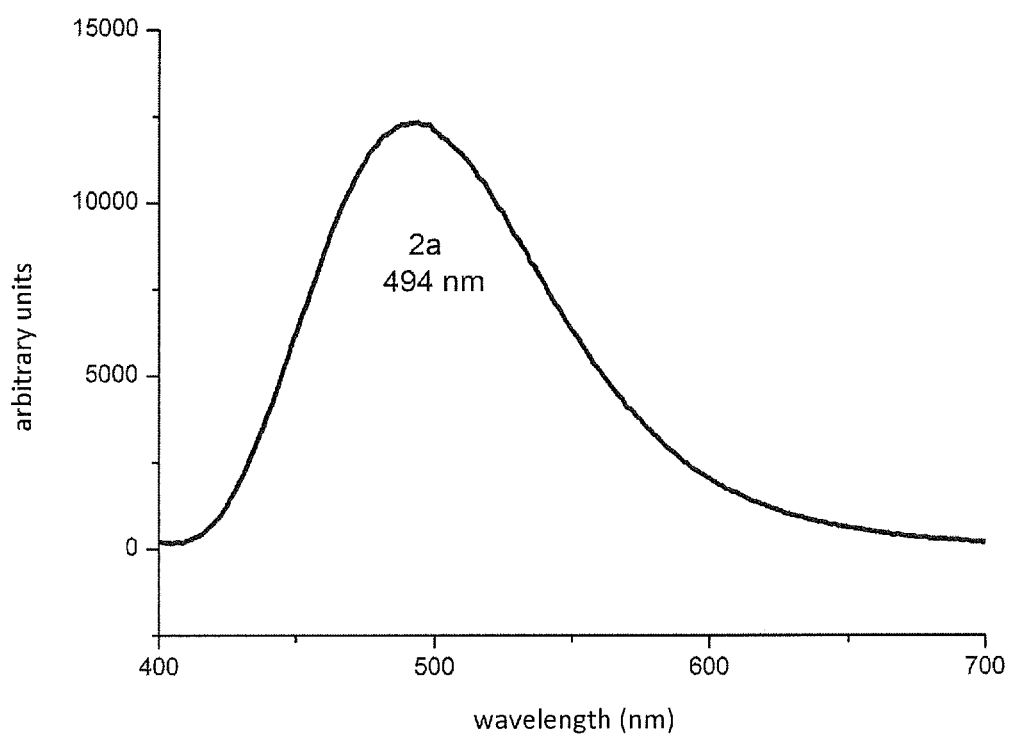

Figure 3: Emission spectrum of 2b:
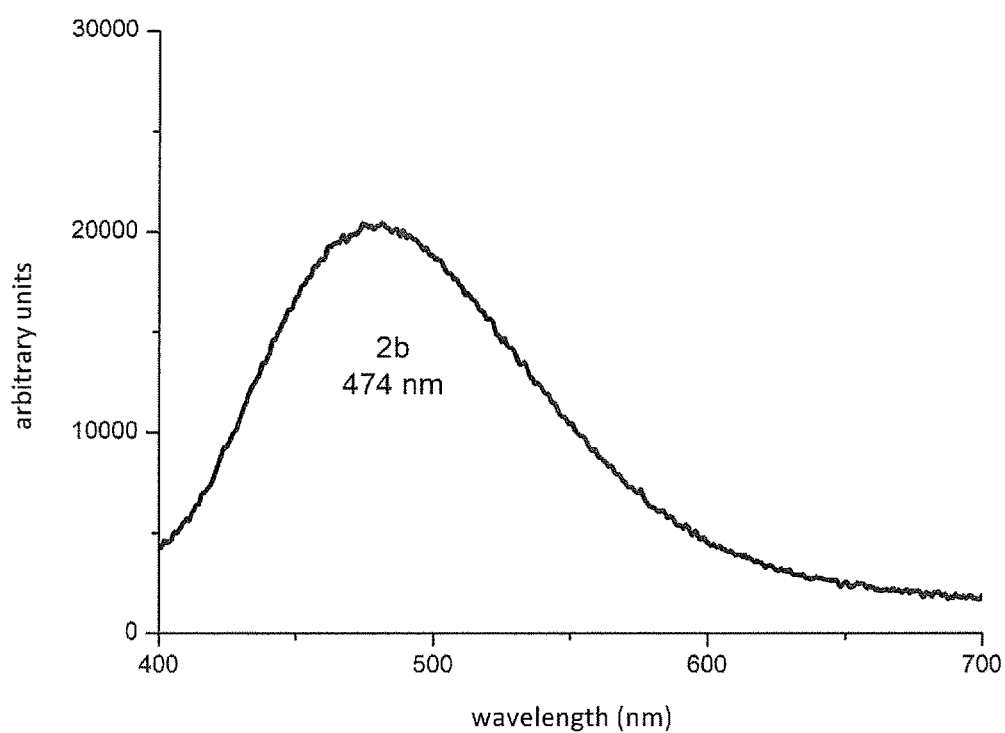

Figure 4: Emission spectrum of 2d:
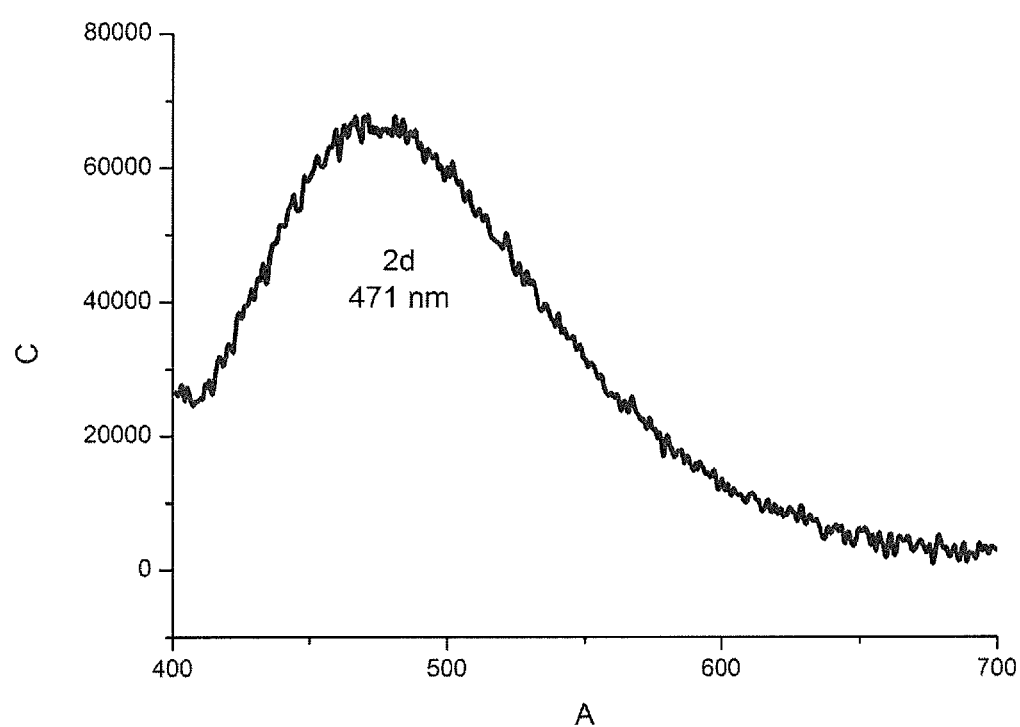

Figure 5: Emission spectrum of 2f:
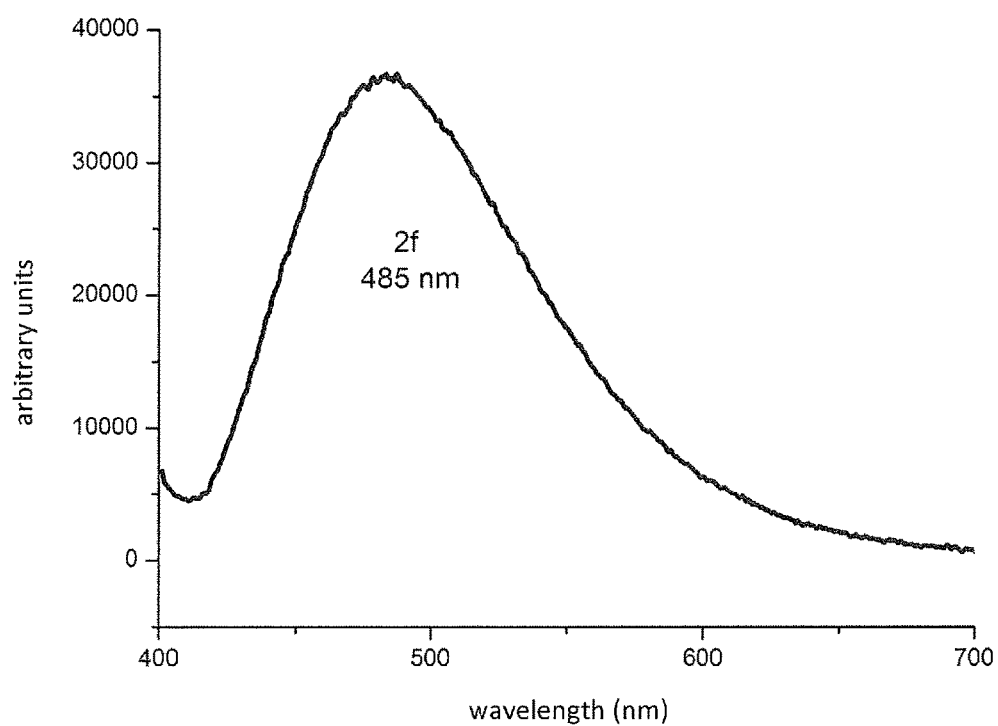

Figure 6: Emission spectrum of 2h:
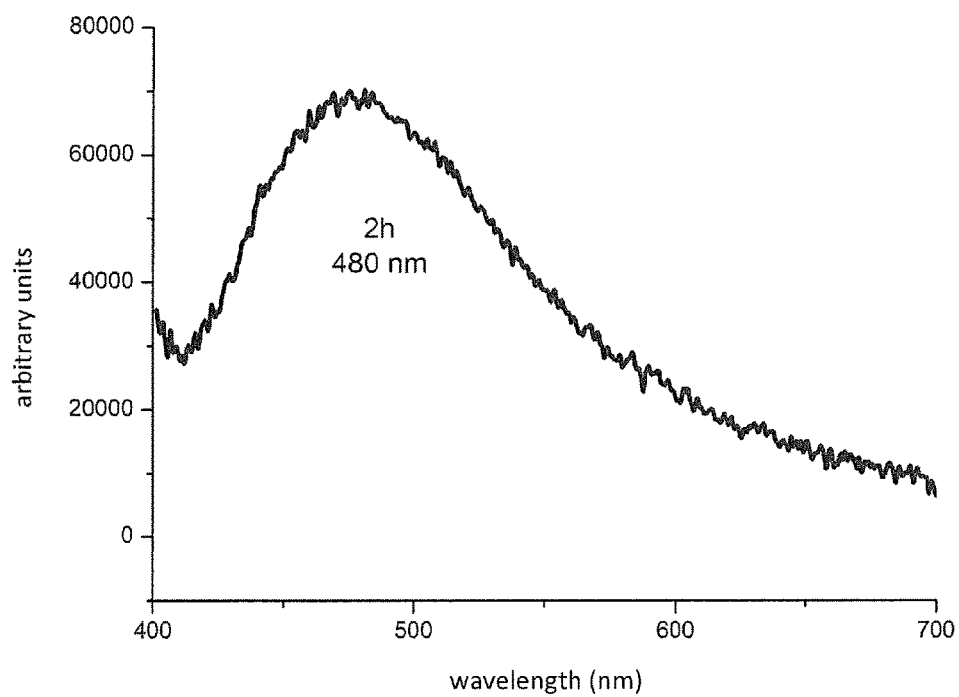

Figure 7: Emission spectrum of 2j:
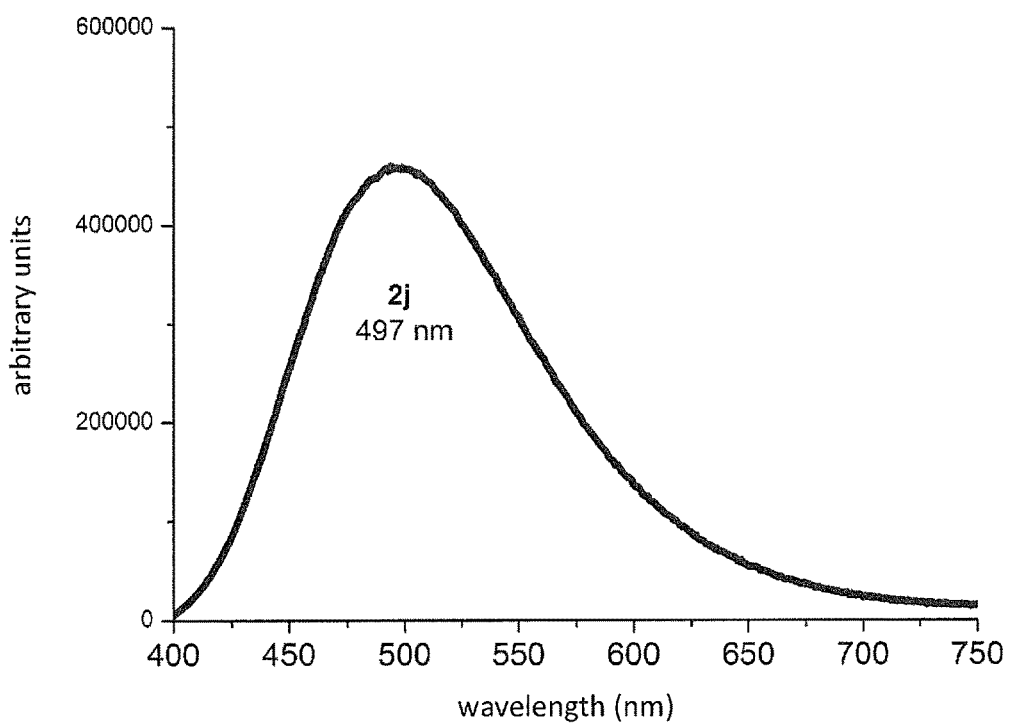

Figure 8: Emission spectrum of 4a:
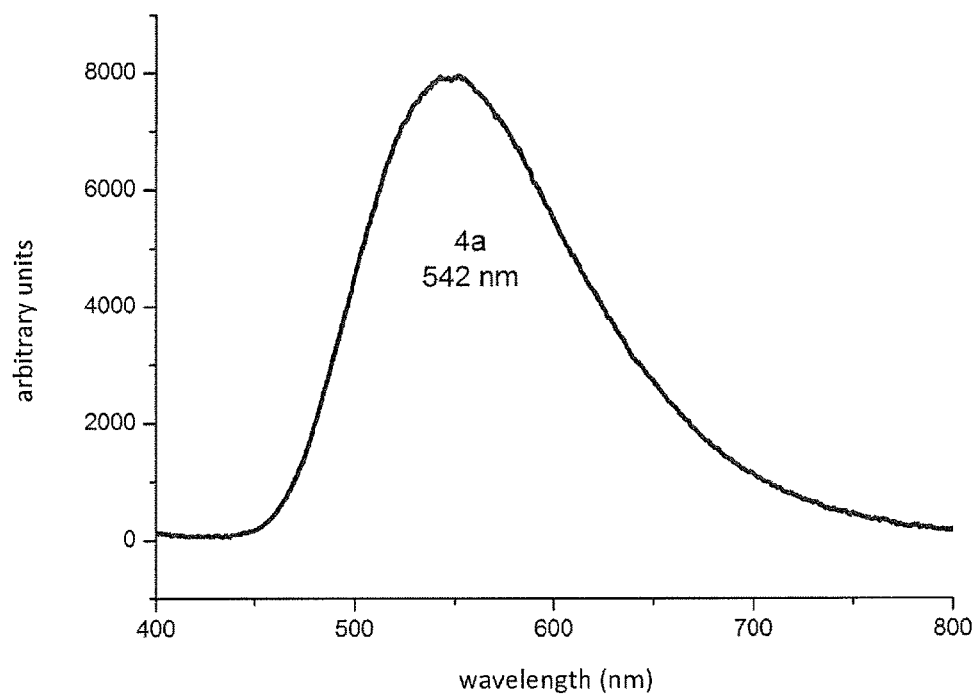

Figure 9: Emission spectrum of 4b:
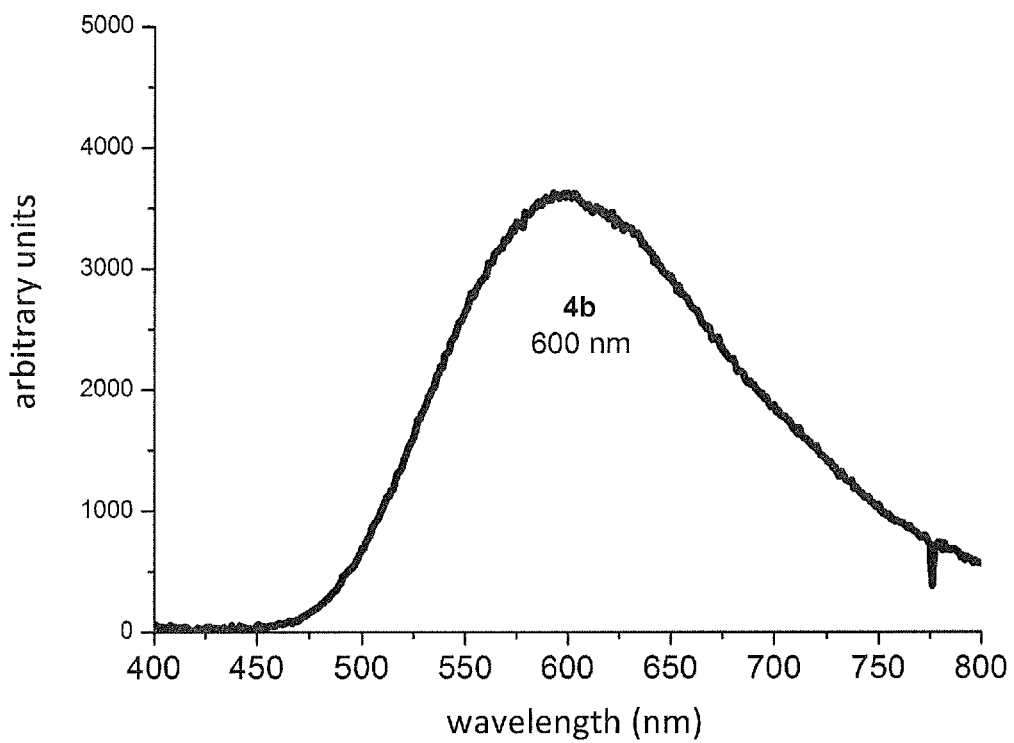

Figure 10: Emission spectrum of 6a:
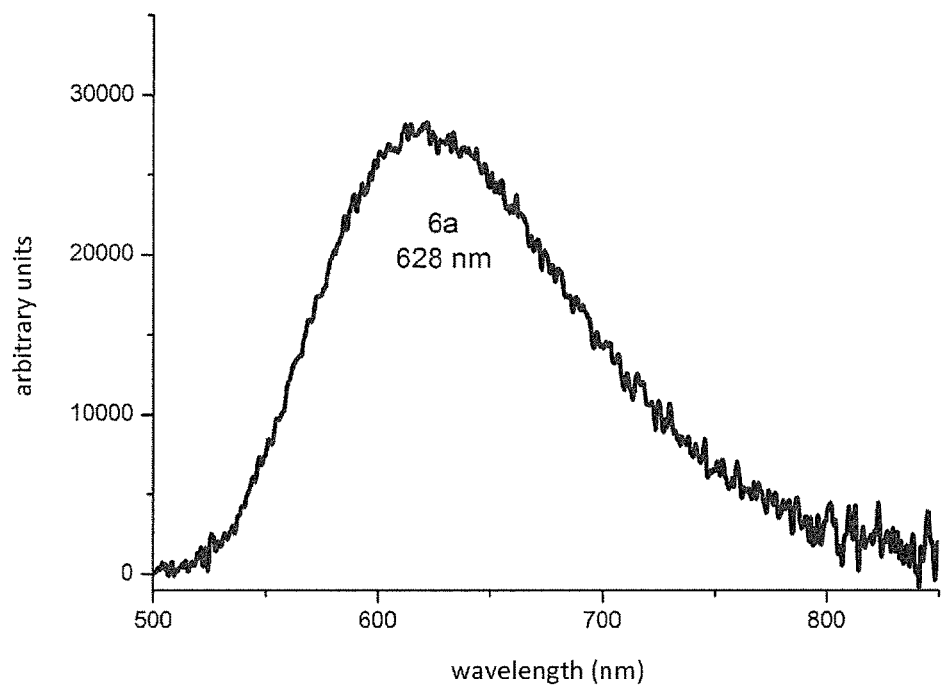

Figure 11: Emission spectrum of 8a:
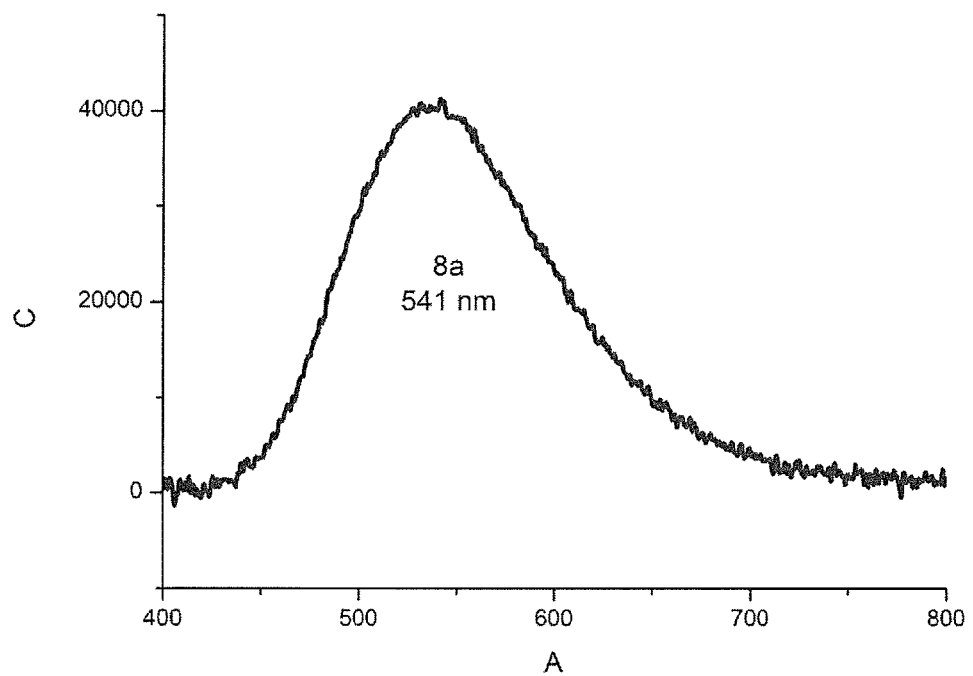

COPPER(I) COMPLEXES, IN PARTICULAR FOR OPTOELECTRONIC COMPONENTS

FIELD OF INVENTION

The invention relates to copper(I) complexes of the general formula A, in particular for use in optoelectronic components.

BACKGROUND OF THE INVENTION

A dramatic change is currently on the horizon in the sector of visual display unit and illumination technology. It will be possible to manufacture flat displays or illuminated surfaces with a thickness of less than 0.5 mm. This new technology is based on the principle of OLEDs, Organic Light Emitting Diodes.

Such components consist predominantly of organic layers. At a voltage of, for example, 5 V to 10 V, negative electrons pass from a conductive metal layer, for example from an aluminum cathode, into a thin electron conduction layer and migrate in the direction of the anode. This consists, for example, of a transparent but electrically conductive thin indium tin oxide layer, from which positive charge carriers, so-called holes, migrate into an organic hole conduction layer. These holes move in the opposite direction compared to the electrons, namely towards the cathode. In a middle layer, the emitter layer, which likewise consists of an organic material, there are additionally special emitter molecules where, or close to which, the two charge carriers recombine and lead to uncharged but energetically excited states of the emitter molecules. The excited states then release their energy as bright emission of light, for example in a blue, green or red color. White light emission is also achievable. In some cases, it is also possible to dispense with the emitter layer when the emitter molecules are present in the hole or electron conduction layer.

Crucial for the construction of effective OLEDs are the light emitting materials (emitter molecules) used. These can be realized in different ways, namely by using purely organic or organometallic molecules as well as complex compounds. It can be shown that the light output of the OLEDs with organometallic substances, so-called triplet emitters can be significantly greater than of purely organic materials. Due to this property, the further development of the organometallic materials is of high significance. Using organometallic complexes with high emission quantum yield (transitions including the lowermost triplet states to the singlet ground states), it is possible to achieve a particularly high efficiency of the device. These materials are often called triplet emitters or phosphorescent emitters.

Against this background, it was the object of the present invention to provide novel compounds, which are suitable for optoelectronic components.

BRIEF DESCRIPTION OF THE DRAWINGS

Exemplary embodiments of the present invention will be described below in more detail, with reference to the accompanying drawings, of which:

FIG. 1 shows the crystal structure of compound 2a.

FIG. 2 shows a graphical overview of the emission spectrum of compound 2a.

FIG. 3 shows a graphical overview of the emission spectrum of compound 2b.

FIG. 4 shows a graphical overview of the emission spectrum of compound 2d.

FIG. 5 shows a graphical overview of the emission spectrum of compound 2f.

FIG. 6 shows a graphical overview of the emission spectrum of compound 2h.

FIG. 7 shows a graphical overview of the emission spectrum of compound 2j.

FIG. 8 shows a graphical overview of the emission spectrum of compound 4a.

FIG. 9 shows a graphical overview of the emission spectrum of compound 4b.

FIG. 10 shows a graphical overview of the emission spectrum of compound 6a.

FIG. 11 shows a graphical overview of the emission spectrum of compound 8a.

DETAILED DESCRIPTION OF EXEMPLARY EMBODIMENTS OF THE INVENTION

Exemplary embodiments of the invention will now be discussed in further detail. This invention may, however, be embodied in many different forms and should not be construed as limited to the embodiments set forth herein.

The problem underlying the invention is solved by the provision of copper(I) complexes of the $Cu_2X_2(E \cap N^*)_3$ form, which have a structure according to formula A:

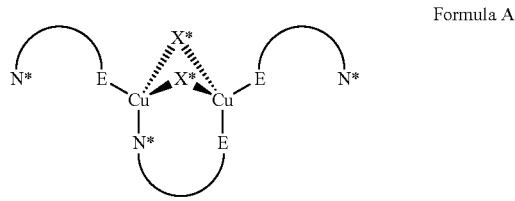

Formula A with:

$X^*$=Cl, Br, I, CN, SCN, akinyl and/or $N_3$ (i.e. independently, such that the complex may have two identical or two different $X^*$ atoms);

$E=R_2As$ and/or $R_2P$;

$N^* \cap E$=bidentate ligands where E=phosphinyl/arsenyl group of the $R_2E$ form (R=alkyl, aryl, alkoxy, phenoxy, amide); $N^*$=imine function. "$\cap$" is a carbon atom. E is in particular a $Ph_2P$ group (Ph=phenyl); the imine function is part of an N-heteroaromatic 5-membered ring such as pyrazole, isoxazole, isothiazole, triazole, oxadiazole, thiadiazole, tetrazole, oxatriazole or thiatriazole. "$\cap$" is likewise part of this aromatic group. The carbon atom is directly adjacent both to the imine nitrogen atom and to the E atom. $N^* \cap E$ may optionally be substituted, in particular by at least one group which increases the solubility of the copper(I) complex in common organic solvents for OLED component production. Common organic solvents comprise, besides alcohols, ethers, alkanes and halogenated aliphatic and aromatic hydrocarbons and alkylated aromatic hydrocarbons, in particular toluene, chlorobenzene, dichlorobenzene, mesitylene, xylene, tetrahydrofuran, phenetole, propiophenone.

A copper(I) complex according to the invention consists in one preferred embodiment of three identical ligands N*∩E, which can act directly as charge transport molecules, whereby different functionalities can be introduced directly via the respective ligands (for example, a hole transport or electron transport unit, hereinafter referred to as hole conductor or electron conductor, respectively) and thus an optimal charge carrier transport to and onto the copper complex is ensured, without having to apply these functionalities via additional units at the periphery of the respective ligands, which reduces the synthesis complexity and hence the costs of preparation. For the same reason, the copper(I) complex according to the invention also preferably comprises identical atoms X*. The great advantage in the case of use of copper as the central metal is its low cost, in particular compared to metals such as Re, Os, Ir, and Pt, which are commonly used in OLED emitters. In addition, the low toxicity of copper is another advantage in support of its use.

Regarding their use in optoelectronic components, the copper(I) complexes according to the invention stand out due to a wide range of achievable emission colors. In addition, the emission quantum yield is high, especially greater than 50%. For emitter complexes with a Cu central ion, the emission decay times are astonishingly short.

In addition, the copper(I) complexes according to the invention are usable in relatively high emitter concentrations without considerable quenching effects. This means that emitter concentrations of 5% to 100% can be used in the emitter layer.

Preferably, the ligands N*∩E are pyrazoles, isoxazoles, isothiazoles, 1,2,4-triazoles, 1,2,4-oxadiazoles, 1,2,4-thiadiazoles, tetrazoles, 1,2,3,4-oxatriazoles and/or 1,2,3,4-thiatriazoles, which each can be substituted as described herein. These ligands can act directly as charge transport molecules whereby different functionalities can be introduced directly via the respective ligand (for example, a hole transport or electron transport unit, hereinafter referred to as hole conductor or electron conductor, respectively) and thus an optimal charge carrier transport to and onto the copper complex is ensured, without having to apply these functionalities via additional units at the periphery of the respective ligands.

Preferably, the ligand N*∩E comprises the following ligands:

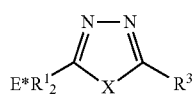

X = NR²: 3E*R¹₂-4R²-5R³-4H-1,2,4-Triazole
X = O: 2E*R¹₂-5R³-1,3,4-Oxadiazole
X = S: 2E*R¹₂-5R³-1,3,4-Thiadiazole

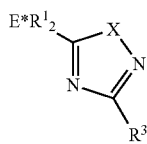

X = NR²: 1R²-3R³-5E*R¹₂-1H-1,2,4-Triazole
X = O: 3R³-5E*R¹₂-1,2,4-Oxadiazole
X = S: 3R³-5E*R¹₂-1,2,4-Thiadiazole

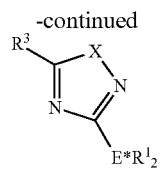

X = NR²: 1R²-3E*R¹₂-5R³-1H-1,2,4-Triazole
X = O: 3E*R¹₂-5R³-1,2,4-Oxadiazole
X = S: 3E*R¹₂-5R³-1,2,4-Thiadiazole

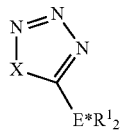

X = NR²: 1R²-5E*R¹₂-1H-Tetrazole
X = O: 5E*R¹₂-1,2,3,4-Oxatriazole
X = S: 5E*R¹₂-1,2,3,4-Thiatriazole

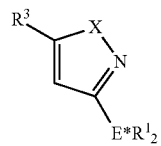

X = NR²: 1R²-3E*R¹₂-5R³-1H-Pyrazole
X = O: 3E*R¹₂-5R³-Isoxazole
X = S: 3E*R¹₂-5R³-Isothiazole
with X = O, S or NR²; E* = As or P;

R1-R3 can be, each independently from each other, hydrogen, halogen or substituents which are bound via oxygen (—OR), nitrogen (—NR₂) or silicon atoms (—SiR₃) as well as alkyl- (also branched or cyclic), aryl, heteroaryl, alkenyl, akinyl groups or substituted alkyl (also branched or cyclic), aryl, heteroaryl and alkenyl groups with substituents such as halogens or deuterium, alkyl groups (also branched or cyclic), and further generally known donor and acceptor groups such as, for example, amines, carboxylates and their esters, and CF₃-groups. R2-R3 can optionally also lead to annulated ring systems.

The invention also relates to a method for producing a copper(I) complex according to the invention. This method according to the invention comprises the step of performing a reaction of N*∩E with Cu(I)X*,
wherein
X*=Cl, Br, I, CN, SCN, Akinyl and/or N₃ (independently from each other);
N*∩E=bidentate ligand with
E=phosphanyl/arsenyl group of the R₂E form (with R=alkyl, aryl, alkoxyl, phenoxyl, or amide);
N*=imine function which is part of an N-heteroaromatic 5-membered ring such as pyrazole, isoxazole, isothiazole, triazole, oxadiazole, thiadiazole, tetrazole, oxatriazole or thiatriazole,
"∩"=at least one carbon atom which is likewise part of the aromatic group, wherein the carbon atom is directly adjacent both to the imine nitrogen atom and to the phosphorus or arsenic atom. The at least one substituent for increasing the solubility of the copper(I) complex in organic solvents, optionally present at the ligand N*∩E, is described further below.

The reaction is performed preferably in dichloromethane (DCM), but other organic solvents such as acetonitrile or tetrahydrofuran or dimethyl sulfoxide or ethanol can also be used. A solid can be obtained by the addition of diethyl ether or hexane or methyl-tert-butylether or pentane or methanol or ethanol or water to the dissolved product. The latter can be conducted by precipitation or inward diffusion or in an ultrasound bath.

In the reaction of bidentate P∩N* ligands (P∩N*=phosphine ligand, definition see below) with Cu(I) X* (X*=Cl, Br, I, CN, SCN, akinyl and/or $N_3$), preferably in dichloromethane (DCM), preferably at room temperature, the binuclear 2:3 complex $Cu_2X^*_2(P\cap N^*)_3$, in which the Cu atoms are bridged by a phosphine ligand as well as the two halide anions, is generated (eq. 1). The other two P∩N* ligands each coordinate only with their phosphorus atoms to one Cu atom each and thereby complete the coordination number of the butterfly-shaped $Cu_2X^*_2$ structure.

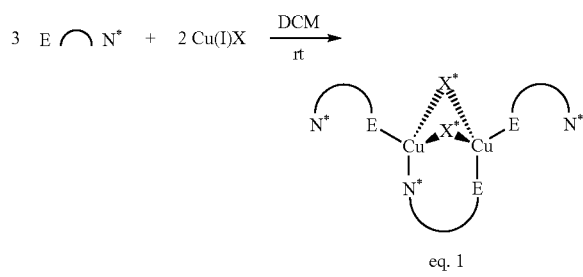

eq. 1

The structure of formula A is related to the known complexes of the form $Cu_2X^*_2L_2L'$ and $Cu_2X^*_2L_4$. In contrast to $Cu_2X^*_2L_2L'$, the complex however is obtainable in only one step through the reaction of Cu(I)X* with the bidentate P∩N* ligand. The complex can be isolated by precipitation with $Et_2O$ as a yellow or red microcrystalline powder. Single crystals can be obtained by slow diffusion of $Et_2O$ into the reaction solution. The identities of the complexes were determined by elemental analyses and X-ray structure analyses.

This structure is reflected bys the general formula A shown above. The bidentate E∩N* ligands can comprise each independently at least one substituent: The substituents can be each independently from each other hydrogen, halogen or substituents which are bound via oxygen (—OR), nitrogen (—$NR_2$) or silicon atoms (—$SiR_3$) as well as alkyl- (also branched or cyclic), aryl, heteroaryl, alkenyl, akinyl groups or substituted alkyl (also branched or cyclic), aryl, heteroaryl and alkenyl groups with substituents such as halogens or deuterium, alkyl groups (also branched or cyclic), and further generally known donor and acceptor groups such as, for example, amines, carboxylates and their esters, and $CF_3$-groups. The substituents can optionally also lead to annulated ring systems.

Solubility

When manufacturing optoelectronic components using wet-chemical processes, it is advantageous to specifically regulate the solubility. Thereby, the complete or partial dissolving of a layer already deposited can be avoided. By introducing special substituents, the solubility characteristics can be strongly influenced. Thereby, it is possible to use orthogonal solvents that dissolve only the substance of the instant manufacturing step, but not the substances of the layer(s) below. For this purpose, the substituents R2-R3 can be selected such that they allow adaptation of the solubilities. The following possibilities for the selection of corresponding substituents are given:

Solubility in Nonpolar Media

Nonpolar substituents R2-R3 increase the solubility in nonpolar solvents and decrease the solubility in polar solvents. Nonpolor groups are, for example, alkyl groups [$CH_3$—($CH_2$)$_n$—] (n=1-30), also branched or cyclic, substituted alkyl groups, e.g. with halogens. Hereby, particularly highlighted are: partly or perfluorinated alkyl groups as well as perfluorinated oligo- and polyether, e.g. [—$(CF_2)_2$—O]$_n$— and (—$CF_2$—O)$_n$— (n=2-500). Further nonpolar groups are: ethers —OR*, thioethers —SR*, differently substituted silanes $R^*_3Si$— (R*=alkyl or aryl), siloxanes $R^*_3Si$—O—, oligosiloxanes $R^{}$(—$R_2Si$—O)$_n$— ($R^{}$=R*, n=2-20), polysiloxanes $R^{**}$(—$R^*_2Si$—O)$_n$— (n>20); oligo/polyphosphazenes $R^{**}$(—$R^*_2P$=N—)$_n$— (n=1-200).

Solubility in Polar Media

Polar substituents R2-R3 increase the solubility in polar solvents. These can be:

alcohol-groups: —OH carboxylic acid, phosphonic acid, sulfonic acid groups as well as their salts and esters (R*=H, alkyl, aryl, halogen; cations: alkali metals, ammonium salts):
—COOH, —P(O)(OH)$_2$, —P(S)(OH)$_2$, —S(O)(OH)$_2$, —COOR*, —P(O)(OR*)$_2$, —P(S)(OR*)$_2$, —S(O)(OR*)$_2$, —CONHR*, —P(O)(NR*$_2$)$_2$, —P(S)(NR*$_2$)$_2$, —S(O)(NR*$_2$)$_2$ sulfoxides: —S(O)R*, —S(O)$_2$R* carbonyl groups: —C(O)R* amines: —$NH_2$, —NR*$_2$, —N($CH_2CH_2OH$)$_2$, hydroxylamines =NOR* oligoesters, —O($CH_2$O—)$_n$, —O($CH_2CH_2$O—)$_n$ (n=2-200)

positively charged substituents: e.g. amminium salts —N$^+$R*$_3$X$^-$, phosphonium salts —P$^+$R*$^3$X$^-$ negatively charged substituents, e.g. borates-(BR*$_3$)$^-$, aluminates-(AlR*$_3$)$^-$ (an alkali metal or ammonium ion can act as anion).

In order to increase the solubility of the copper(I) complexes according to the invention in organic solvents, optionally at least one of the structures N*∩E is substituted preferably with at least one substituent. The substituent can be selected from the group consisting of:

long-chained, branched or unbranched or cyclic alkyl chains with a length of C1 to C30, preferably with a length of C3 to C20, particularly preferred with a length of C5 to C15, long-chained, branched or unbranched or cyclic alkoxy chains with a length of C1 to C30, preferably with a length of C3 to C20, particularly preferred with a length of C5 to C15, branched or unbranched or cyclic perfluoro alkyl chains with a length of C1 to C30, preferably with a length of C3 to C20, particularly preferred with a length of C5 to C15, and short-chained polyethers, such as, for example, polymers in the form of (—$OCH_2CH_2O$—)$_n$, with n<500. Examples are polyethylene glycols (PEG), which can be applied as chemical inert, watersoluble and non-toxic polymers with a chain length of 3-50 repeating units.

In one preferred embodiment of the invention, the alkyl chains or alkoxy chains or perfluoro alkyl chains are modified by polar groups, e.g. by alcohols, aldehydes, acetals, amines, amidines, carboxylic acids, carboxylic acid esters, carboxylic acid amides, imides, carboxylic acid halides, carboxylic acid anhydrides, ethers, halogens, hydroxamic acid, hydrazines, hydrazones, hydroxyl amines, lactones, lactams, nitriles, isocyanides, isocyanates, isothiocyanates, oximes, nitrosoaryls, nitroalkyls, nitroaryls, phenols, phosphoric acid esters and/or phosphonic acid, thiols, thioethers, thioaldehydes, thioketones, thioacetals, thiocarboxylic acids, thioester, dithio acid, dithio acid ester, sulfoxides, sulfones, sulfonic acid, sulfonic acid esters, sulfinic acid, sulfinic acid esters, sulfenic acid, sulfenic acid esters, thiosulfinic acid, thiosulfinic acid esters, thiosulfonic acid, thiosulfonic acid esters, sulfonamides, thiosulfonamides, sulfinamides, sulfenamides, sulfates, thiosulfates, sultones, sultames, trialkylsilyl and triarylsilyl groups as well as trialkoxysilyl groups, which lead to an additional increase in solubility.

A very distinct increase in solubility is achieved with a unit that is at least a C3 unit, branched or unbranched, or cyclic. Substitution e.g. with a linear C3 chain (see below) leads to a very good solubility, for example, in dichlorobenzene and to a good solubility in chlorobenzene and toluene.

Optionally, the method of preparation comprises the step that at least one ligand N*∩E is substituted with at least one substituent for increasing the solubility in the desired organic solvent, wherein the substituent is selected in one embodiment of the invention from the groups described above.

Copper(I) complexes of the invention are also complexes which can be prepared by such a synthesis method.

The copper(I) complexes of formula A can be applied according to the invention as emitters in an emitter layer of a light emitting optoelectronic component. The optoelectronic components are preferably the following: organic light emitting components (OLEDs), light emitting electrochemical cells, OLED-sensors (in particular in gas and vapor sensors which are not hermetically sealed from the outside), organic solar cells, organic field-effect transistors, organic lasers, and down-conversion elements.

According to the invention, the copper(I) complexes of formula A can also be applied as absorber materials in an absorber layer of an optoelectronic component.

The term "optoelectronic components" refers in particular to:
organic light emitting components (organic light emitting diodes, OLEDs)
light emitting electrochemical cells (LECs, LEECs),
OLED-sensors, in particular in gas and vapor sensors, which are not hermetically sealed from the outside,
organic solar cells (OSCs, organic photovoltaics, OPVs),
organic field-effect transistors and
organic lasers.

In one embodiment of the invention, the ratio of the copper(I) complex in the emitter layer or absorber layer in such an optoelectronic component is 100%. In an alternative embodiment, the ratio of the copper(I) complex in the emitter layer or absorber layer is 1% to 99%.

Preferably, the concentration of the copper(I) complex as emitter in optical light emitting components, particularly in OLEDs, is between 1% an 99%, preferably between 1% and 80%.

In another aspect, the present invention also refers to optoelectronic components which comprise a copper(I) complex as described herein. Thereby, the optoelectronic component can be an organic light emitting component, an organic diode, an organic solar cell, an organic transistor, as an organic light emitting diode, a light emitting electrochemical cell, an organic field-effect transistor, or an organic laser.

In a method for the preparation of an optoelectronic component, in which a copper(I) complex of the invention is used, the application of such a copper(I) complex on a carrier material can be performed. This application can be carried out by wet-chemical means, by means of colloidal suspension or by means of sublimation, preferably by wet-chemical means. The method may comprise the following steps:

Depositing a first emitter complex dissolved in a first solvent onto a carrier, and depositing a second emitter complex dissolved in a second solvent on the carrier; wherein the first emitter complex is not soluble in the second solvent, and the second emitter complex is not soluble in the first solvent; and wherein the first emitter complex and/or the second emitter complex is/are a copper(I) complex according to the invention. The method can further comprise the following step: Depositing a third emitter complex dissolved in a first solvent or in a third solvent on the carrier, wherein the third complex is a copper(I) complex according to the invention, wherein the first and the second solvent are not identical.

Another aspect of the invention relates to a method for altering the emission and/or absorption properties of an electronic component. Thereby, a copper(I) complex according to the invention is introduced into a matrix material for conducting electrons or holes into an optoelectronic component.

Another aspect of the invention relates to the use of a copper(I) complex according to the invention, particularly in an optoelectronic component, for the conversion of UV radiation or of blue light to visible light, especially to green, yellow or red light (down-conversion).

In another aspect, the invention relates to a bidentate ligand of formula B, in particular for the production of a copper complex of formula A, as well as the method for the preparation of such a ligand.

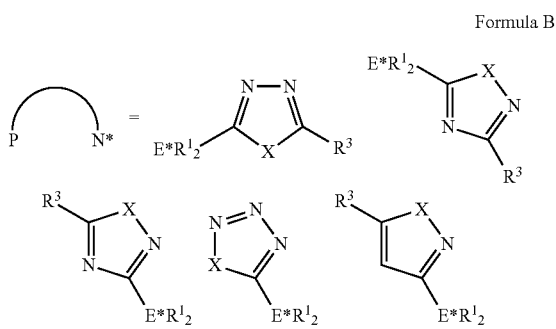

Formula B

The symbols used in formula B correspond to the symbols used in formula A, which are described herein.

The method for preparing a bidentate ligand of formula B is performed according to the scheme shown below:

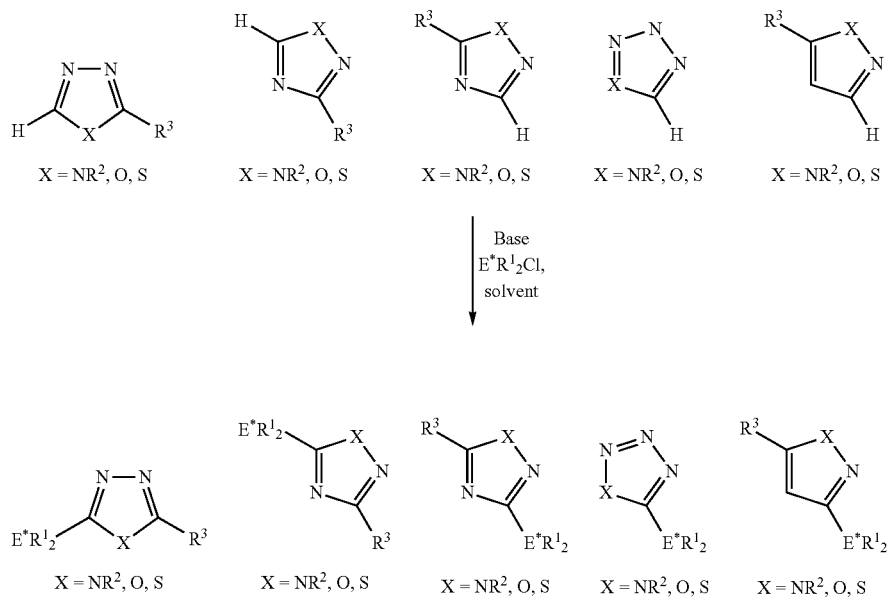

Examples

In the examples shown here, the ligand E∩N* of the general formula A is a ligand P∩N* (with E=Ph$_2$P).

The bidentate phosphine ligands pyrazole, isoxazole, isothiazole, triazole, oxadiazole, thiadiazole, tetrazole, oxatriazole, thiatriazole were used for the preparation of the copper complexes according to the description above:

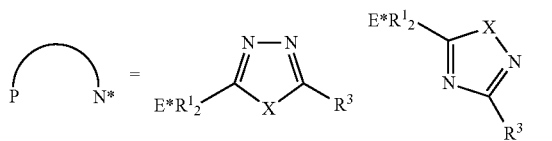

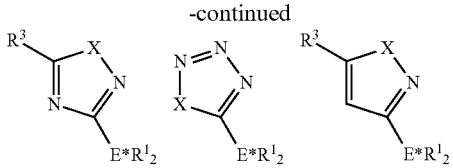

-continued

The ligands were synthesized in the case of the pyrazoles, triazoles, oxadiazoles, thiadiazoles, tetrazoles partially according to literature, whereas the isoxazoles, isothiazoles, oxatriazoles and thiatriazoles are not yet known in literature and thus they were synthesized according to a new synthesis which is shown below:

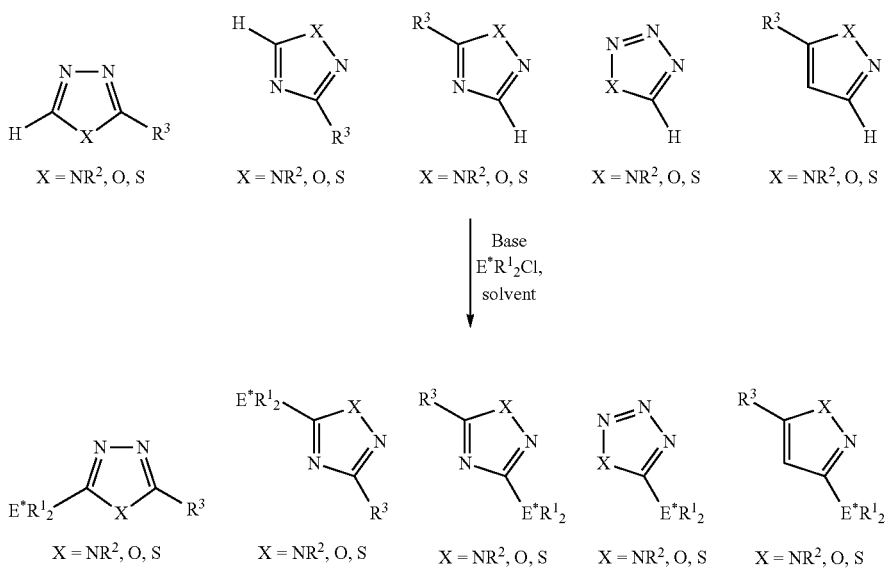

The symbols used in the scheme above correspond to the symbols used for formula A and ligands E∩N*, which are described above.

The identities of the ligands were determined by NMR spectroscopy and mass spectroscopy.

Examples for Complexes of the Form Cu₂X*₂(P∩N*)₃

I. P∩N*=Ph₂Ptriaz, 1a-k: Cu₂I₂(Ph₂Ptriaz)₃, 2a-k

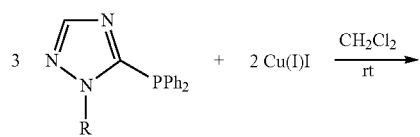

R = Butyl 1a,
Propyl 1b,
Pentyl 1c,
Hexyl 1d,
Isobutyl 1e,
Isopropyl 1f,
Phenethyl 1g,
2EtHex 1h,
Methyl 1i,
Benxyl 1j,
4-Nitrophenyl 1k

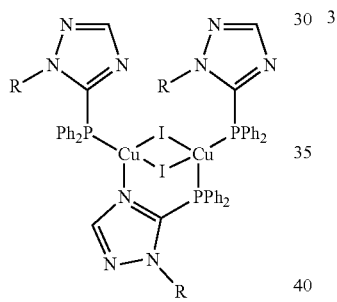

R = Butyl 2a,
Propyl 2b,
Pentyl 2c,
Hexyl 2d,
Isobutyl 2e,
Isopropyl 2f,
Phenethyl 2g,
2EtHex 2h,
Methyl 2i,
Benzyl 2j,
4-Nitrophenyl 2k The compounds 2a-j are white, fine-crystalline solids, compound 2k is an orange-colored solid.
Characterization: elemental analysis:

| | |
|---|---|
| 2a (R = butyl) | calc.: C 49.55; H 4.62; N 9.63 |
| | found: C 49.45; H 4.62; N 9.41 |
| 2b (R = propyl) | calc.: C 48.35; H 4.30; N 9.95 |
| | found: C 48.10; H 4.27; N 10.06 |
| 2c (R = pentyl) | calc.: C 50.67; H 4.92; N 9.33 |
| | found: C 50.52; H 4.86; N 9.16 |
| 2d (R = hexyl) | calc.: C 51.73; H 5.21; N 9.05 |
| | found: C 51.47; H 5.09; N 8.80 |
| 2e (R = isobutyl) | calc.: C 49.55; H 4.62; N 9.63 |
| | found: C 49.16; H 4.50; N 9.38 |
| 2f (R = isopropyl) | calc.: C 48.35; H 4.30; N 9.95 |
| | found: C 47.30; H 4.28; N 9.71 |
| 2g (R = phenethyl) | calc.: C 56.26; H 4.72; N 8.20 (x1 Cyclohexan) |
| | found: C 56.13; H 4.89; N 8.02 |
| 2h (R = 2EtHex) | calc.: C 52.56; H 5.64; N 8.29 (x0.5 CH₂Cl₂) |
| | found: C 52.68; H 5.60; N 8.32 |
| 2i (R = methyl) | calc.: C 41.74; H 3.43; N 9.32 (x2 CH₂Cl₂) |
| | found: C 42.00; H 3.73; N 8.93 |
| 2j (R = benzyl) | calc.: C 53.63, H 3.86; N 8.93 |
| | found: C 53.25; H 3.81; N 8.73 |
| 2k (R = 4-nitrophenyl) | calc.: C 46.11, H 2.98; N 10.58 |
| | found: C 46.30; H 2.99; N 10.50 |

The crystal structure of 2a is shown in FIG. 1.

The emission spectra of 2a, 2b, 2d, 2f, 2h, 2j are shown in FIG. 2-7.

The photoluminescence (PL)-quantum yield of 2a is 80% (measured with Hamamatsu C9920-02G).

II. P∩N*=Ph₂Poxadiaz, 3a-b: Cu₂I₂(Ph₂Poxadiaz)₃, 4a-b

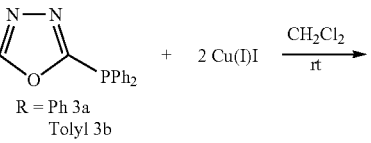

R = Ph 3a
Tolyl 3b

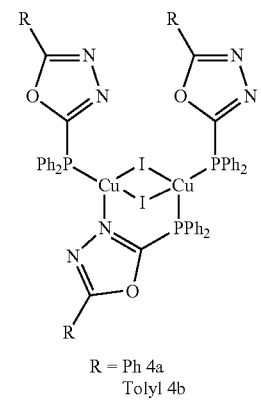

R = Ph 4a
Tolyl 4b

Compounds 4a and 4b are yellow, fine-crystalline solids.
Characterization: elemental analysis:

| | |
|---|---|
| 4a (R = Ph) | calc.: C 52.53; H 3.31; N 6.13 |
| | found: C 52.64; H 3.68; N 5.73 |
| 4b (R = tolyl) | calc.: C 53.53; H 3.64; N 5.94 |
| | found: C 53.90; H 3.68; N 5.86 |

The emission spectra of 4a and 4b are shown in FIGS. 8 and 9.

The PL-quantum yield of 4a is 63% and the PL-quantum yield of 4b is 65% (measured with Hamamatsu C9920-02G)

III. P∩N*=Ph₂Pthiadiaz, 5a: Cu₂I₂(Ph₂Pthiadiaz)₃, 6a

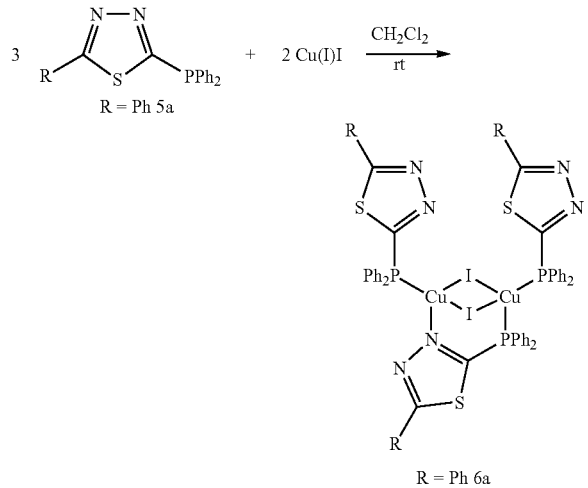

Compound 6a is a yellow, fine-crystalline solid.
Characterisation: elemental analysis:

| 6a (R = Ph) | calc.: C 45.18; H 3.07; N 5.02; S 5.74 (x3 CH₂Cl₂) |
| --- | --- |
| | found: C 45.58; H 3.00; N 5.02; S 5.78 |

The emission spectrum of 6a is shown in FIG. 10.

IV. P∩N*=Ph₂PBntetrazole, 7a: Cu₂I₂(Ph₂PBntetrazole)₃, 8a

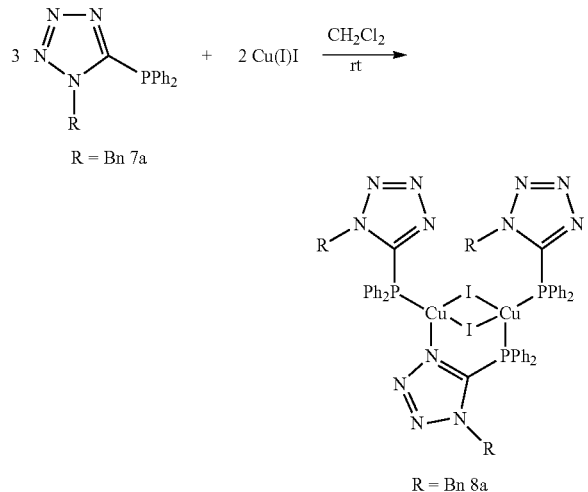

Compound 8a is a white, fine-crystalline solid.
Characterization: elemental analysis:

| 8a (R = Bn) | calc.: C 50.97; H 3.64; N 11.89 |
| --- | --- |
| | found: C 50.81; H 3.57; N 11.68 |

The emission spectrum of 8a is shown in FIG. 11.
Since in the compounds 2a to 8a, only one identical bidentate ligand is applied in a ratio of Cu:(N*∩E)=2:3 (E=As, P), extremely intense luminescent complexes of formula A are obtained in a single step in high yields. Thereby, the complexity of synthesis is reduced.

The copper(I) complexes according to the invention are characterized in particular by an emission towards the blue or into the blue emission range.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:
1. A copper(I) complex of formula A:

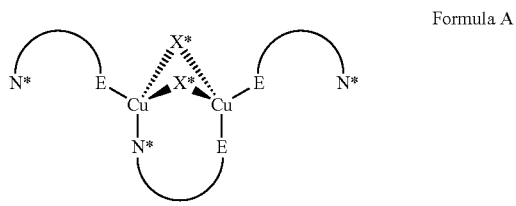

Formula A wherein:
X* is selected from the group consisting of Cl, Br, I, CN, SCN, akinyl and N₃; and
N*∩E is a bidentate ligand wherein
  E is a phosphanyl/arsenyl group of the R₂E form, wherein R is selected from the group consisting of alkyl, aryl, alkoxyl, phenoxyl and amide,
  N* is an imine-function which is part of an N-heteroaromatic 5-membered ring selected from the group consisting of pyrazole, isoxazole, isothiazole, triazole, oxadiazole, tetrazole, oxatriazole and thiatriazole,
  ∩ is at least one carbon atom, which is part of the N-heteroaromatic group, wherein the at least one carbon atom being directly adjacent both to the imine nitrogen atom and to the phosphorus or arsenic atom.
2. The copper (I) complex of claim 1, wherein N*∩E comprises at least one substituent for increasing the solubility of the copper(I) complex in an organic solvent.
3. The copper(I) complex according to claim 2, wherein the at least one substituent for increasing solubility is selected from the group consisting of branched or unbranched or cyclic long-chained alkyl chains with a length of C1 to C30, branched or unbranched or cyclic long-chained alkoxy chains with a length of C1 to C30, branched or unbranched or cyclic long-chained perfluoro alkyl chains with a length of C1 to C30, and short-chained polyethers with a chain length of 3-50 repeating units.
4. The copper(I) complex of claim 1, wherein N*∩E is selected from the group consisting of

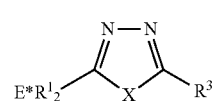

X = NR²: 3E*R¹₂—4R²—5R³-4H-1,2,4-Triazole
X = O: 2E*R¹₂—5R³-1,3,4-Oxadiazole

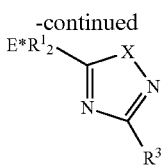

X = NR²: 1R²—3R³—5E*R¹₂-1H-1,2,4-Triazole
X = O: 3R³—5E*R¹₂-1,2,4-Oxadiazole

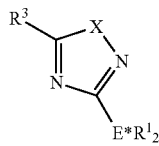

X = NR²: 1R²—3E*R¹₂—5R³-1H-1,2,4-Triazole
X = O: 3E*R¹₂—5R³-1,2,4-Oxadiazole

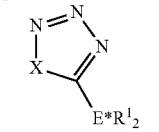

X = NR²: 1R²—5E*R¹₂-1H-Tetrazole
X = O: 5E*R¹₂-1,2,3,4-Oxatriazole
X = S: 5E*R¹₂-1,2,3,4-Thiatriazole

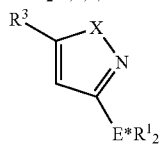

X = NR²: 1R²—3E*R¹₂—5R³-1H-Pyrazole
X = O: 3E*R¹₂—5R³-Isoxazole
X = S: 3E*R¹₂—5R³-Isothiazole wherein:
X is selected from the group consisting of O, S and NR²;
E* is As or P; and
R1-R3 are independently selected from the group consisting of hydrogen, halogen, substituents bound via oxygen (—OR), nitrogen (—NR₂), silicon atoms (—SiR₃), alkyl- (branched or cyclic), aryl, heteroaryl, alkenyl, akinyl groups, substituted alkyl (branched or cyclic), aryl, heteroaryl and alkenyl groups with substituents selected from the group consisting of halogens or deuterium, alkyl groups (branched or cyclic), and donor and acceptor groups selected from the group consisting of amines, carboxylates and their esters, and CF₃-groups.

5. The copper(I) complex of claim 4, wherein R2-R3 lead to annulated ring systems.

6. The copper (I) complex of formula A according to claim 4, wherein the bidentate ligand has the formula B:

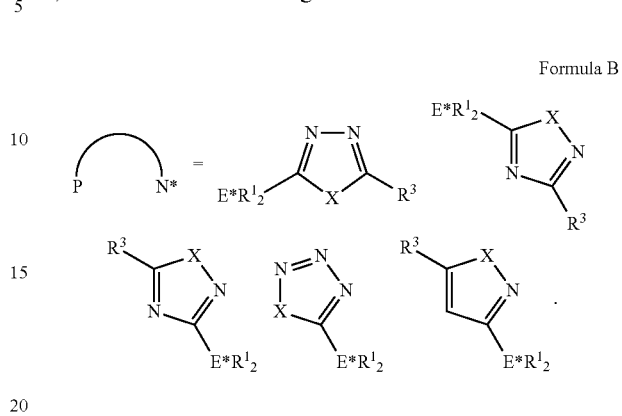

Formula B

7. The copper(I) complex of claim 1, wherein the copper (I) complex is used as an emitter or an absorber in an optoelectronic component.

8. The copper(I) complex of claim 7, wherein the optoelectronic component is selected from the group consisting of organic light emitting components (OLEDs), light emitting electrochemical cells, OLED-sensors, in particular gas and vapor sensors which are not hermetically sealed from the outside, organic solar cells, organic field-effect transistors, organic lasers, and down conversion elements.

9. The copper(I) complex of claim 7, wherein the concentration of the copper(I) complex as the emitter in the optical light emitting component is between 1% and 80%.

10. An optoelectronic component comprising the copper (I) complex of claim 1, shaped as a component selected from the group consisting of organic light emitting component, organic diode, organic solar cell, organic transistor, organic light emitting diode, light emitting electrochemical cell, organic field-effect transistor, and organic laser.

11. The copper(I) complex of claim 1, wherein the copper (I) complex is used in an optoelectronic component for converting UV radiation or blue light to visible light.

12. The copper(I) complex of claim 11, wherein the copper(I) complex is used in the optoelectronic component for converting UV radiation or blue light to at least one of green, yellow and red light.

* * * * *